(12) United States Patent
DeStefano et al.

(10) Patent No.: US 11,974,780 B2
(45) Date of Patent: May 7, 2024

(54) DEVICES, SYSTEMS, AND METHODS FOR TREATING AN ECTOPIC PREGNANCY WITHOUT COMPROMISING THE PREGNANCY

(71) Applicant: Covidien LP, Mansfield, MA (US)

(72) Inventors: Lisa M. DeStefano, Eliot, ME (US); Alaena D. Maiorano, Huntington Beach, CA (US)

(73) Assignee: Covidien LP, Mansfield, MA (US)

( * ) Notice: Subject to any disclaimer, the term of this patent is extended or adjusted under 35 U.S.C. 154(b) by 575 days.

(21) Appl. No.: 17/142,820

(22) Filed: Jan. 6, 2021

(65) Prior Publication Data
US 2021/0236169 A1    Aug. 5, 2021

Related U.S. Application Data

(60) Provisional application No. 62/968,453, filed on Jan. 31, 2020.

(51) Int. Cl.
    *A61B 17/42*      (2006.01)
    *A61B 17/00*      (2006.01)

(52) U.S. Cl.
    CPC ........ *A61B 17/42* (2013.01); *A61B 17/00234* (2013.01); *A61B 2017/00358* (2013.01); *A61B 2017/4216* (2013.01)

(58) Field of Classification Search
CPC . A61B 17/00234; A61B 17/42; A61B 17/435; A61B 2017/00358; A61B 2017/306; A61B 2017/4216; A61B 2017/4233
See application file for complete search history.

(56) References Cited

U.S. PATENT DOCUMENTS

| | | |
|---|---|---|
| 5,360,389 A | 11/1994 | Chenette |
| 6,010,448 A | 1/2000 | Thompson |
| 6,610,005 B1 | 8/2003 | Tao |
| 9,282,995 B2 | 3/2016 | Carson et al. |
| 10,188,426 B2 | 1/2019 | Sillender |
| 2003/0032896 A1 | 2/2003 | Bosley et al. |
| 2009/0270789 A1* | 10/2009 | Maxymiv .......... A61B 17/0218 604/272 |
| 2014/0221735 A1* | 8/2014 | Californiaa ............ C12M 21/06 600/34 |

* cited by examiner

*Primary Examiner* — Mohamed G Gabr

(74) *Attorney, Agent, or Firm* — Carter, DeLuca & Farrell LLP

(57) ABSTRACT

A method of treating an ectopic pregnancy without compromising the pregnancy includes inserting a surgical device trans-vaginally to a position outside a uterus such that a portion of the surgical device is positioned adjacent a gestational sac, including an embryo, that is disposed outside the uterus. The method further includes atraumatically capturing the gestational sac with the surgical device, atraumatically moving the surgical device to relocate the captured gestational sac to a position within the uterus, atraumatically releasing the gestational sac from the surgical device within the uterus, and withdrawing the surgical device.

16 Claims, 7 Drawing Sheets

DEVICES, SYSTEMS, AND METHODS FOR TREATING AN ECTOPIC PREGNANCY WITHOUT COMPROMISING THE PREGNANCY

CROSS-REFERENCE TO RELATED APPLICATIONS

This application claims the benefit of, and priority to, U.S. Provisional Patent Application No. 62/968,453, filed on Jan. 31, 2020, the entire contents of which are hereby incorporated herein by reference.

FIELD

The present disclosure relates to surgical devices, systems, and methods. More particularly, the present disclosure relates to devices, systems, and methods for treating an ectopic pregnancy without compromising the pregnancy.

BACKGROUND

An ectopic pregnancy occurs when an embryo is located in an abnormal location, i.e., somewhere other than the uterus. In the vast majority of ectopic pregnancies, the gestational sac containing the embryo does not travel through the fallopian tube and into the uterus to implant in the endometrial lining of the uterus but, rather, remains within the fallopian tube, continuing to grow and develop therein.

If not naturally resolved, an ectopic pregnancy may result in various symptoms, usually presenting six to eight weeks after conception, including uncharacteristic pelvic discomfort and pain. Note: for women known to be at-risk for ectopic pregnancies, and therefore monitored more closely, the gestational sac may be visible as early as 3 weeks. The continued growth of the embryo causes a life-threatening condition that requires medical intervention to save the mother's life. If not timely and properly treated, internal bleeding, for example, from a ruptured fallopian tube may occur. In fact, ectopic pregnancies cause the majority of first-trimester maternal deaths and account for between 3% and 10% of all maternal pregnancy-related deaths.

Currently available treatments for ectopic pregnancy are: 1) if early enough in the pregnancy, injection of an abortifacient drug, e.g. methotrexate, to stop the embryo's growth whereby, after necrosis, the embryo is absorbed into the body or miscarried; or 2) if later in the pregnancy, surgery to remove the embryo from the body and, if irreparably damaged, to also remove the fallopian tube. Both of these treatment options result in loss of the pregnancy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a method of treating an ectopic pregnancy without compromising the pregnancy including inserting a surgical device trans-vaginally to a position outside a uterus such that a portion of the surgical device is positioned adjacent a gestational sac, including an embryo, that is disposed outside the uterus. The method further includes atraumatically capturing the gestational sac with the surgical device, atraumatically moving the surgical device to relocate the captured gestational sac to a position within the uterus, atraumatically releasing the gestational sac from the surgical device within the uterus, and withdrawing the surgical device.

In an aspect of the present disclosure, the position outside the uterus is within a fallopian tube. In such aspects, inserting the surgical device includes inserting the portion of the surgical device through the uterus and into the fallopian tube. Further, in such aspects, atraumatically moving the surgical device includes moving the portion of the surgical device from the fallopian tube into the uterus.

In another aspect of the present disclosure, atraumatically releasing the gestational sac from the surgical device within the uterus includes releasing the gestational sac towards an endometrial lining of the uterus.

In still another aspect of the present disclosure, atraumatically releasing the gestational sac from the surgical device within the uterus includes urging the gestational sac into contact with an endometrial lining of the uterus.

In yet another aspect of the present disclosure, atraumatically capturing the gestational sac includes partially or fully retaining the gestational sac within a transport cavity defined within the surgical device.

In still yet another aspect of the present disclosure, after inserting the surgical device and prior to atraumatically capturing the gestational sac, the method includes transitioning the surgical device from a collapsed condition to an at least partially expanded condition.

In another aspect of the present disclosure, after atraumatically releasing the gestational sac and before withdrawing the surgical device, the method includes transitioning the surgical device from the at least partially expanded condition to the collapsed condition.

In yet another aspect of the present disclosure, after inserting the surgical device and prior to atraumatically capturing the gestational sac, the method includes transitioning the surgical device from a collapsed condition to an expanded, at least partially inverted condition.

In still another aspect of the present disclosure, after atraumatically releasing the gestational sac and before withdrawing the surgical device, the method includes transitioning the surgical device from the expanded, at least partially inverted condition to the collapsed condition.

In another aspect of the present disclosure, atraumatically capturing the gestational sac is facilitated via generating a vacuum within a portion of the surgical device by a vacuum source. Additionally, or alternatively, atraumatically releasing the gestational sac is facilitated by releasing a vacuum from a portion of the surgical device.

A device for treating an ectopic pregnancy without compromising the pregnancy provided in accordance with the present disclosure includes a shaft assembly and an end effector assembly extending distally from the shaft assembly. The end effector assembly includes a frame transitionable from a collapsed condition to an expanded condition to an expanded, inverted condition. The frame is encapsulated in an elastic jacket including a portion extending over a distal end of the end effector assembly. With the end effector assembly disposed in the expanded, inverted condition, vacuum applied through the shaft assembly pulls the portion of the elastic jacket at least partially into an interior of the frame to define a transport cavity configured for receipt of a gestational sac including an embryo.

In an aspect of the present disclosure, the shaft assembly includes an inner shaft and an outer shaft, and the frame assembly includes a proximal end portion fixed relative to the outer shaft and a distal end portion fixed relative to the inner shaft. In such aspects, relative movement between the inner and outer shafts transitions the frame from the collapsed condition to the expanded condition to the expanded, inverted condition.

In another aspect of the present disclosure, the frame is formed from a wire mesh.

In still another aspect of the present disclosure, the transport cavity defines an interior surface lined by the portion of the elastic jacket and/or has a semi-ovoid shape.

Another device for treating an ectopic pregnancy without compromising the pregnancy provided in accordance with the present disclosure includes an outer sheath, an elastic jacket sealed about an open distal end of the outer sheath, an inner shaft slidably disposed within the outer sheath, and an end effector assembly fixed relative to a distal end portion of the inner shaft. The end effector assembly is transitionable between a collapsed condition within the outer sheath and an expanded condition extending distally from the outer sheath in response to relative movement between the outer sheath and the inner shaft. In the expanded condition, the end effector assembly stretches the elastic jacket to expand radially outwardly.

In an aspect of the present disclosure, the end effector assembly includes a frame having a plurality of petals.

In another aspect of the present disclosure, with the end effector assembly disposed in the expanded condition, vacuum applied through the outer sheath pulls a portion of the elastic jacket at least partially into an interior of the end effector assembly to define a transport cavity configured for receipt of a gestational sac including an embryo. In such aspects, the transport cavity may define an interior surface lined by the portion of the elastic jacket and/or have a conical shape.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
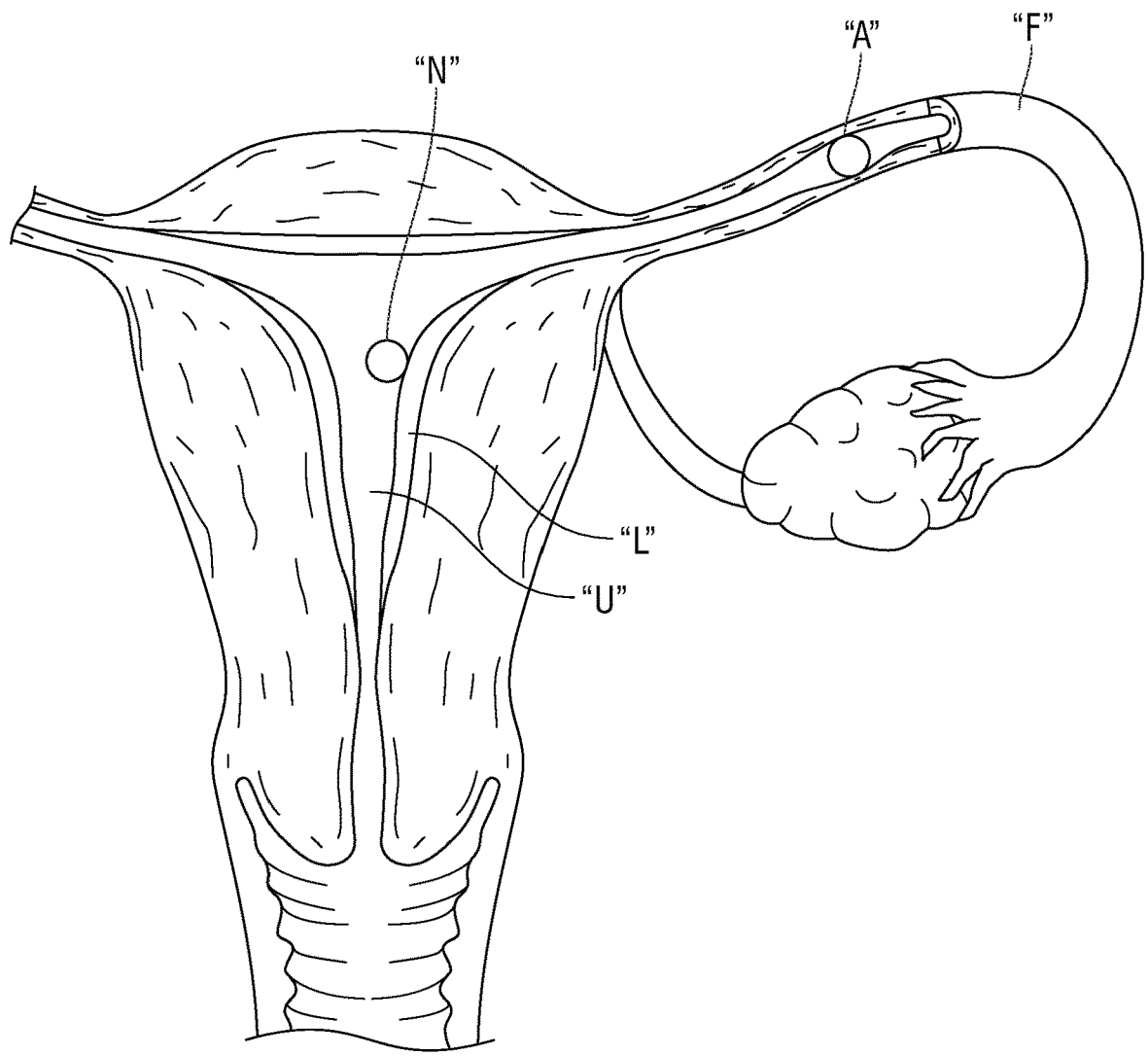
FIG. 1 is an illustration of a portion of the reproductive anatomy of a pregnant human female.

Referring to FIG. 1, an ectopic pregnancy occurs when a gestational sac "G" including a human embryo "E" (see FIG. 2) implants in an abnormal place, i.e., somewhere other than the uterus "U." For example, and as is most common in ectopic pregnancies, the gestational sac "G" (FIG. 2) may not travel through the fallopian tube "F" and into the uterus "U" for implantation therein (e.g., at a normal location "N") but, rather, may remain in the fallopian tube "F," continuing to grow and develop therein (e.g., at an abnormal location "A"). With additional reference to FIG. 2, the gestational sac "G" includes an outer amnion membrane "M" filled with amniotic fluid "AF" and containing the embryo "E" and yolk sac "Y" (which is attached to the embryo "E") therein.

Figure 2:
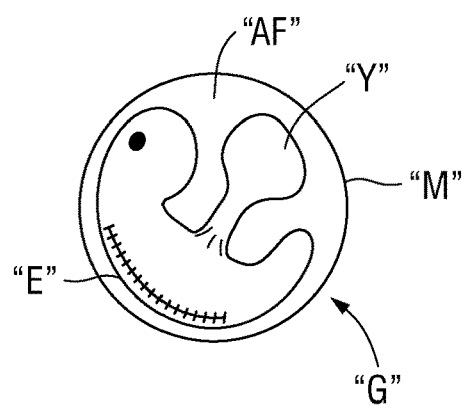
FIG. 2 is an illustration of a gestational sac containing an embryo at an early stage of development.

Continuing with reference to FIGS. 1 and 2, in order to treat an ectopic pregnancy without compromising the pregnancy, the present disclosures provides devices, systems, and methods for: atraumatic capture of the gestational sac "G," e.g., from the abnormal location "A" within the fallopian tube "F" or other abnormal location; atraumatic transport of the gestational sac "G" from the abnormal location "A" to an appropriate location, e.g., to the normal location "N" within the uterus "U;" and atraumatic release of the gestational sac "G" at the normal location "N" to allow the embryo "E" within the gestational sac "G" to implant within the endometrial lining "L" of the uterus "U" and continue to grow and develop as the pregnancy progresses.

Figure 3:
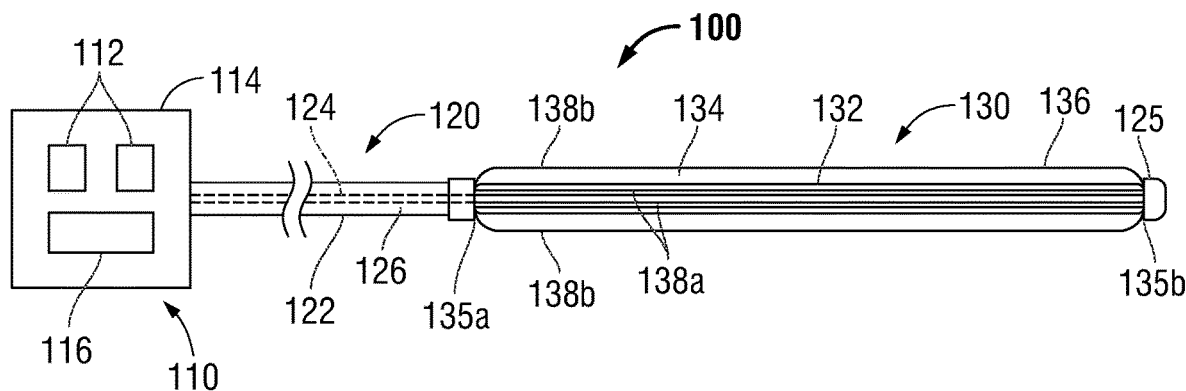
FIG. 3 is a side, cross-sectional view of an ectopic pregnancy treatment device provided in accordance with the present disclosure and shown in a collapsed condition.
Figure 4:
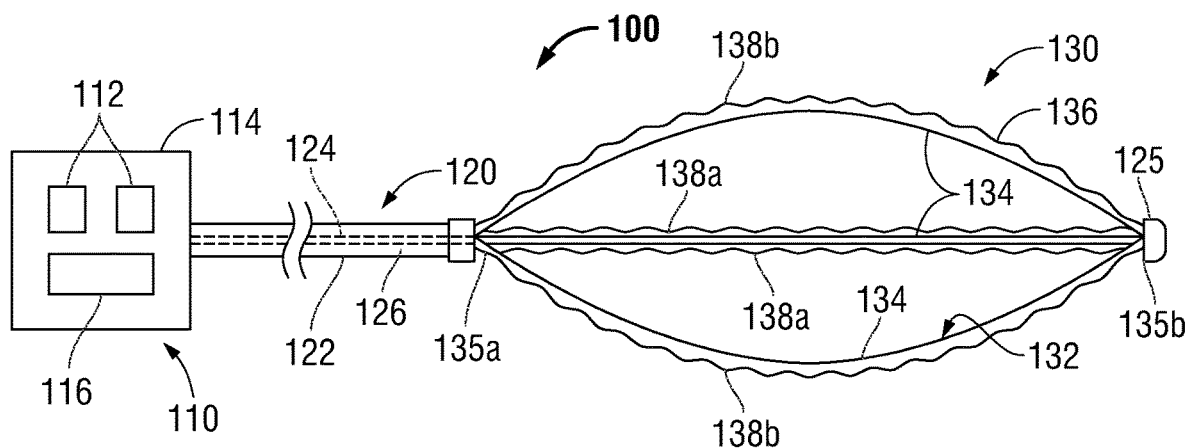
FIG. 4 is a side, cross-sectional view of the ectopic pregnancy treatment device of FIG. 3, shown in a partially-expanded condition.
Figure 5:
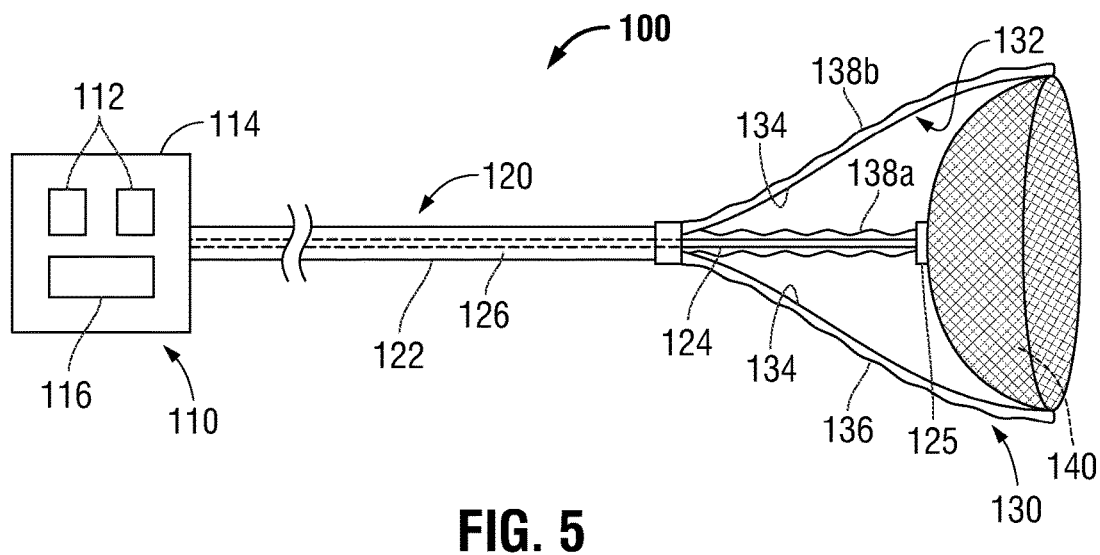
FIG. 5 is a side, cross-sectional view of the ectopic pregnancy treatment device of FIG. 3, shown in an expanded, inverted condition with suction applied to establish a transport cavity.

FIGS. 3-5 illustrate an ectopic pregnancy treatment device 100 provided in accordance with the present disclosure. Device 100 generally includes a control assembly 110 including one or more controls 112, a shaft assembly 120 extending distally from control assembly 110, and an end effector assembly 130 disposed at a distal end portion of shaft assembly 120. Control assembly 110 may include a housing 114 configured for manual grasping and manipulation and/or configured to attach to a robotic arm (not shown) for robotic manipulation of device 100. The one or more controls 112 of control assembly 110 may be disposed on or within housing 114, or may be remote therefrom, and are configured to enable selective actuation of the various features of device 100, as detailed below. Controls 112 may be mechanical, e.g., levers, sliders, wheels, triggers, joysticks, etc., configured to actuate manual drive mechanisms, or may be electrical, e.g., switches, GUI's, dials, etc., configured to actuated powered drive mechanisms. Control assembly 110 may further include or be adapted to connect to a vacuum source 116, e.g., a vacuum pump, with one or more of the controls 112 configured to control activation, deactivation, and/or operational parameters of the vacuum source 116.

Shaft assembly 120 includes an outer support shaft 122 and an inner actuation shaft 124. Outer support shaft 122 may be at least partially articulable (e.g., flexible and/or malleable) to, for example, facilitate insertion of outer support shaft 122 trans-vaginally, through the uterus "U," and into a fallopian tube "F" (see FIG. 1). Outer support shaft 122 may be passively articulable, e.g., via external forces or manipulation, or may be actively articulable, e.g., via a cable-driven system (not shown) incorporated into outer support shaft 122 and control assembly 110. Outer support shaft 122 further defines an internal lumen 126 adapted to connect to vacuum source 116 to enable the application of suction through internal lumen 126.

Inner actuation shaft 124 is slidably disposed within outer support shaft 122 and includes a proximal end portion coupled to one of the controls 112 of control assembly 110 and a distal end portion 125 that extends through end effector assembly 130 and is coupled thereto at a distal end portion 135b thereof. As such, actuation of the control 112 associated with inner actuation shaft 124 pulls inner actuation shaft 124 proximally through and relative to outer support shaft 122 to thereby transition end effector assembly 130 between a collapsed condition (FIG. 3), a partially-expanded condition (FIG. 4), and an expanded, inverted condition (FIG. 5). Alternatively, or additionally, outer support shaft 122 may be configured to slide distally about inner actuation shaft 124 to achieve one or more of the collapsed condition (FIG. 3), the partially-expanded condition (FIG. 4), or the expanded, inverted condition (FIG. 5).

Continuing with reference to FIGS. 3-5, end effector assembly 130 includes an expandable and at least partially invertable frame 132 and an elastic jacket 136 encapsulating frame 132 therein. Frame 132 may be formed from a resilient mesh 134, e.g., of braided nitinol wire, or may define any other suitable configuration. Frame 132 is fixed at its proximal end portion 135a to a distal end portion of outer support shaft 122 and at its distal end portion 135b to distal end portion 125 of inner actuation shaft 124. In this manner, actuation of inner actuation shaft 124 relative to outer support shaft 122 manipulates, e.g., expands, inverts, etc., frame 132. Elastic jacket 136 includes an inner layer 138a and an outer layer 138b that cooperate to encapsulate frame 132 therebetween within a sealed, e.g., air-tight interior volume.

Referring to FIG. 3, with inner actuation shaft 124 disposed in a distally-extend position relative to outer support shaft 122, end effector assembly 130 is disposed in a collapsed condition wherein frame 132 is elongated and defines a minimum diameter. This collapsed condition facilitates insertion and withdrawal of end effector assembly 130. Turning to FIG. 4, in order to transition end effector assembly 130 to the partially-expanded condition, inner actuation shaft 124 is pulled proximally relative to outer support shaft 122. As a result of this movement, and since proximal end portion 135a of frame 132 is fixed to outer support shaft 122 and distal end portion 135b of frame 132 is fixed to inner actuation shaft 124, the distal end portion 135b of frame 132 is moved towards the proximal end portion 135a thereof, causing frame 132 to resiliently expand radially outwardly while shortening in length.

With additional reference to FIG. 5, upon further proximal pulling of inner actuation shaft 124 relative to outer support shaft 122, distal end portion 135b of frame 132 is eventually inverted into the proximal end portion 135a of frame 132 such that frame 132 defines a semi-ovoid. With frame 132 disposed in this expanded, inverted condition, outer layer 138b of elastic jacket 136 extends about and defines a generally planar, distally-facing surface of the inverted, semi-ovoid frame 132. Upon application of vacuum through outer support shaft 122, e.g., via activation of vacuum source 116, negative pressure is established within the interior volume defined by semi-ovoid frame 132, thereby suctioning the portion of outer layer 138b of elastic jacket 136 that previously defined the generally planar, distally-facing surface of the inverted, semi-ovoid frame 132 into frame to define a transport cavity 140 having a semi-ovoid shape (with outer layer 138b defining a concave inner surface of transport cavity 140). The amount of vacuum applied and/or the extent of inversion of frame 132 may be varied, as required, to define a suitable configuration, e.g., diameter, depth, etc., of transport cavity 140 for atraumatic receipt, retention, and protection of a gestational sac "G" (FIG. 2) therein.

In order to return end effector assembly 130 to its initial, collapsed condition, e.g., after transporting and releasing the gestational sac "G" (FIG. 2) via controlled release of the vacuum and relaxation of elastic jacket 136, inner actuation shaft 124 is returned distally relative to outer support shaft 122 to elongate and resiliently collapse frame 132 back to the condition illustrated in FIG. 3, thus facilitating removal.

Figure 11:
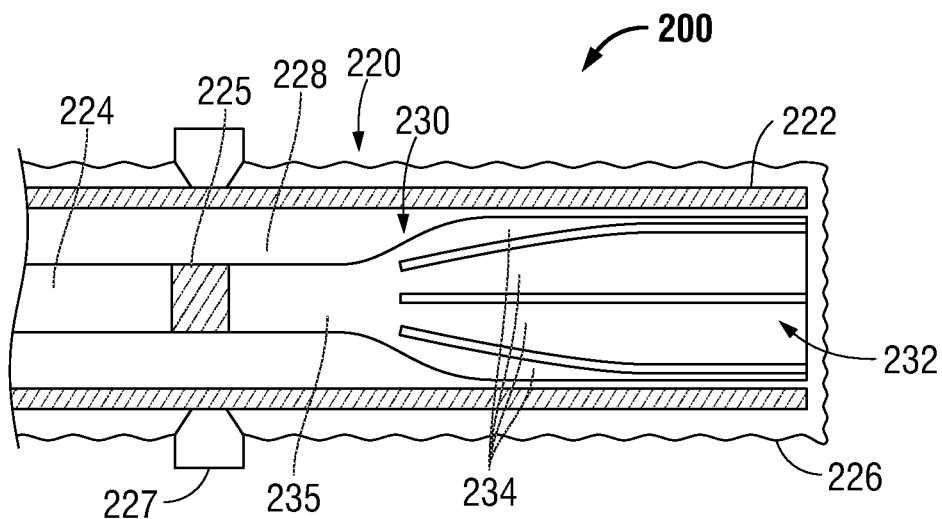
FIG. 11 is a side, cross-sectional view of another ectopic pregnancy treatment device provided in accordance with the present disclosure and shown in a collapsed condition.
Figure 12:
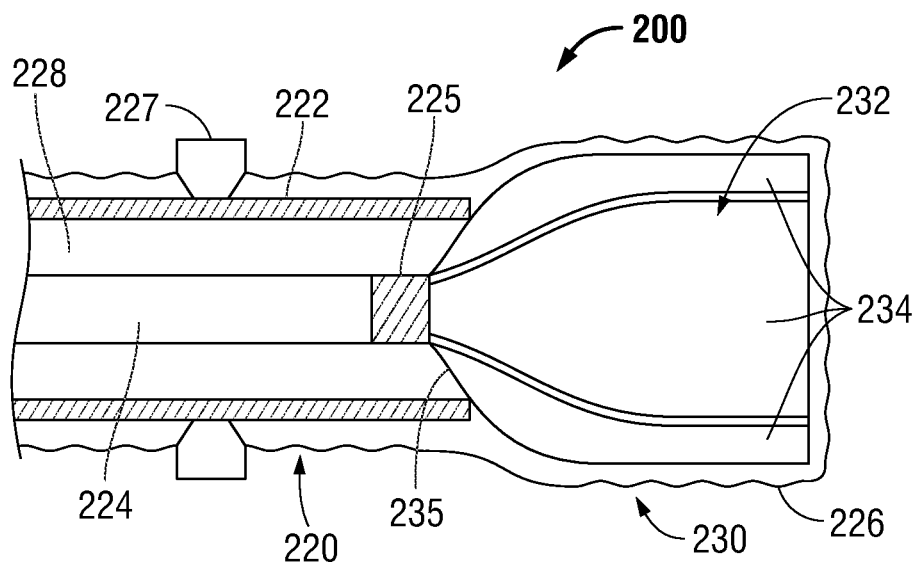
FIG. 12 is a side, cross-sectional view of the ectopic pregnancy treatment device of FIG. 11 shown in an expanded condition.

Turning to FIGS. 6-10, in conjunction with FIGS. 3-5, use of device 100 for treating an ectopic pregnancy without comprising the pregnancy includes the atraumatic capture, transport, and release of a gestational sac "G" from a location within a fallopian tube "F" to a location within the uterus "U" adjacent the endometrial lining "L" to enable implantation and continued growth of the embryo "E" as the pregnancy progresses. "Atraumatic" as utilized herein refers to an action or actions that maintain viability of the gestational sac "G" (including the embryo "E" and other matter therein) without inflicting irreversible damage thereupon. Although described with respect to device 100, the method detailed hereinbelow is also contemplated for performance with any other suitable device or devices, e.g., device 200 (FIGS. 11 and 12).

Figure 6:
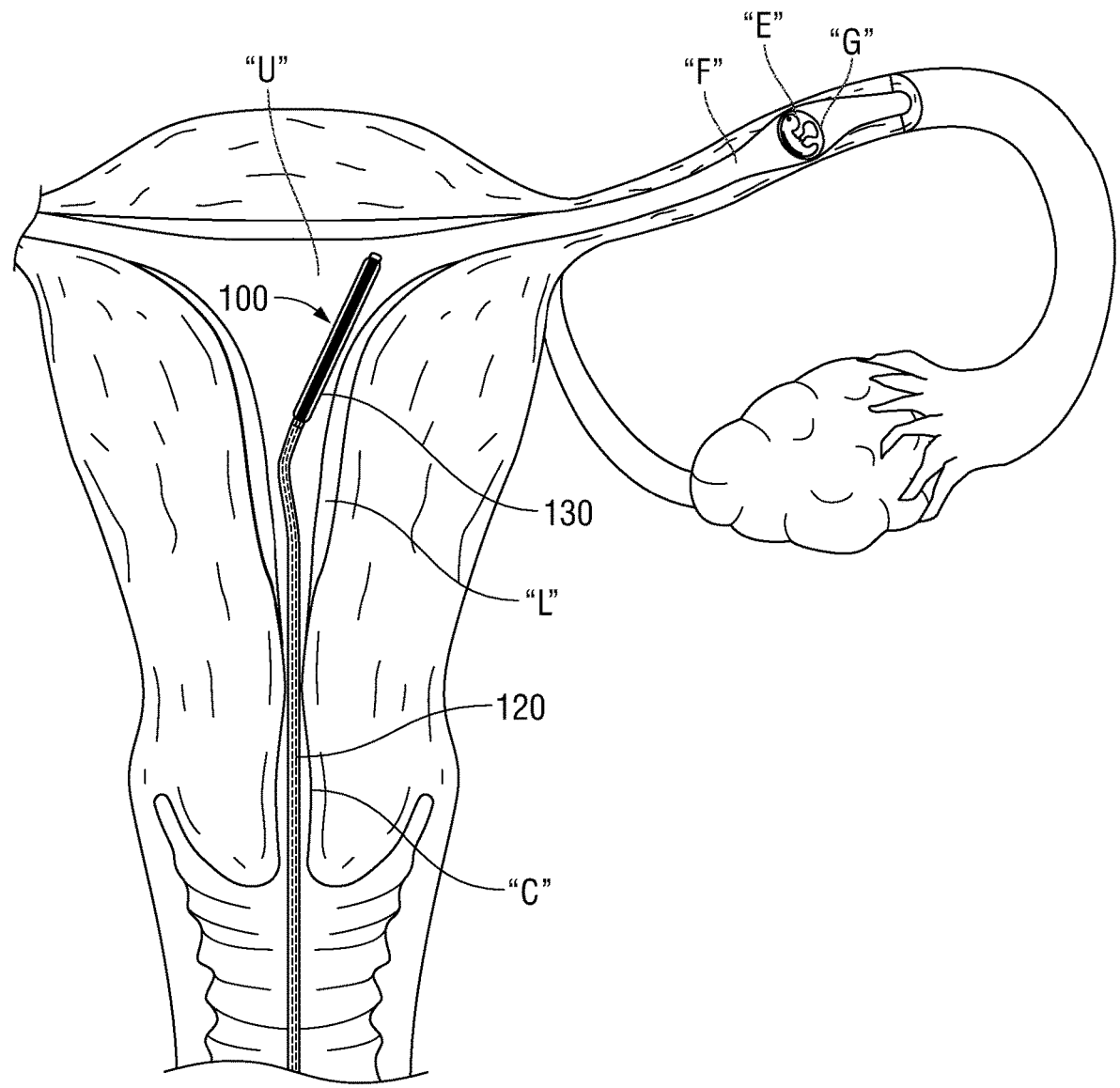
FIGS. 6 is an illustration of the ectopic pregnancy treatment device of FIG. 3 being inserted trans-vaginally through the uterus of a pregnant female to treat an ectopic pregnancy.

Referring initially to FIG. 6, in conjunction with FIGS. 3-5, with end effector assembly 130 disposed in the collapsed condition, device 100, lead by end effector assembly 130, is inserted trans-vaginally, through the cervix "C" and the uterus "U" and into the fallopian tube "F" to a position adjacent the gestational sac "G."

Figure 7:
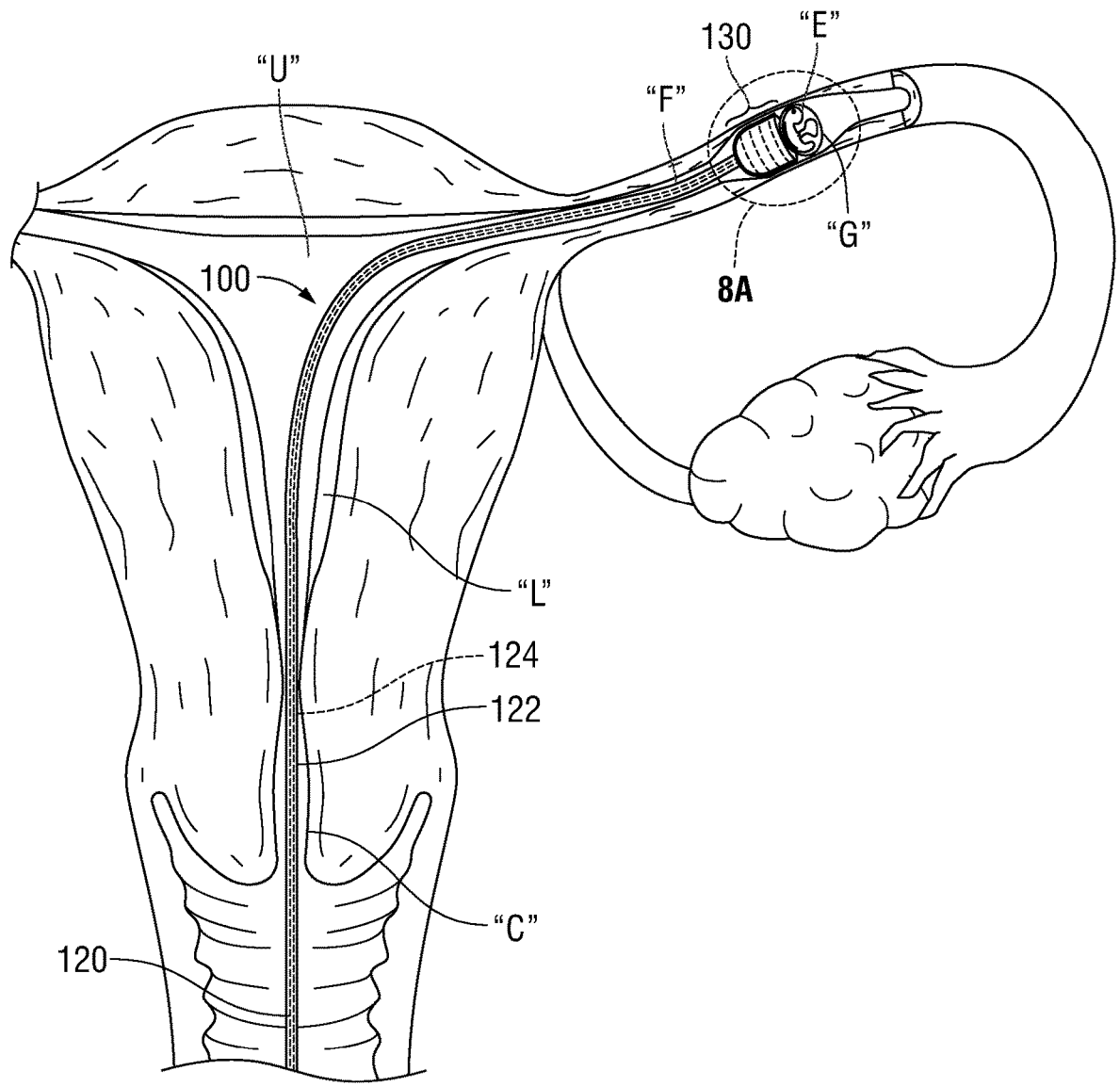
FIG. 7 is an illustration of the ectopic pregnancy treatment device of FIG. 3 positioned with the a fallopian tube of a pregnant female to capture the gestational sac, including the embryo, therein.
Figure 8A:
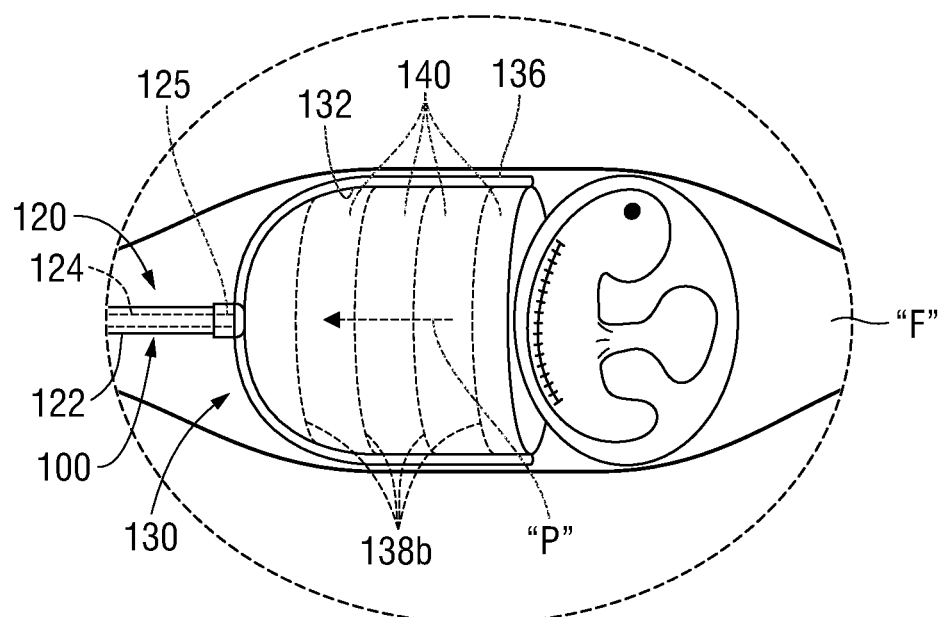
FIG. 8A is an enlarged view of the area of detail identified as "8A" in FIG. 7, wherein the gestational sac is partially received within the ectopic pregnancy treatment device of FIG. 3.
Figure 8B:
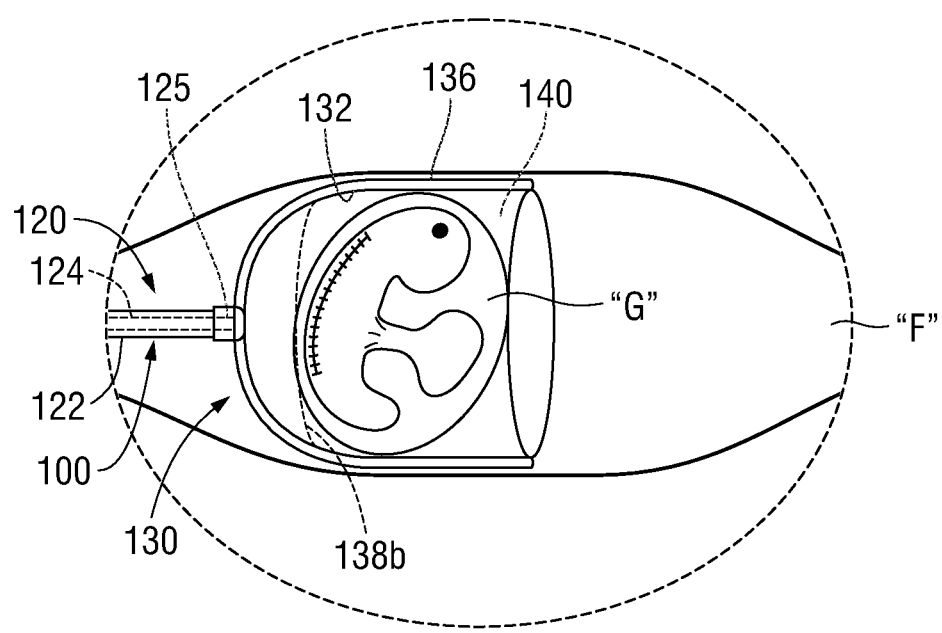
FIG. 8B is an enlarged view of the area of detail identified as "8A" in FIG. 7, wherein the gestational sac is fully received within the ectopic pregnancy treatment device of FIG. 3.

Once this position has been achieved, and with additional reference to FIGS. 7, 8A, and 8B, end effector 130 is transitioned from the collapsed condition (FIGS. 3 and 6), through the partially-expanded condition (FIG. 4) to the expanded, inverted condition. Prior, after, overlapping, or simultaneously with the application of vacuum through outer support shaft 122, e.g., via activation of vacuum source 116 (FIGS. 3-5), end effector assembly 130 is advanced distally relative to the gestational sac "G" such that, as a result of this distal movement and the applied vacuum establishing transport cavity 140 within the inverted, semi-ovoid frame 132, the gestational sac "G" is atraumatically drawn into and captured within the transport cavity 140. In other embodiments, end effector assembly 130 is not moved distally but is held substantially stationary during the application of vacuum. As noted above, the amount of vacuum applied and extent of inversion of frame 132 may be controlled to suitably form transport cavity 140 for atraumatic receipt, retention, and protection of the gestational sac "G" therein. More specifically, as more vacuum is applied, outer layer 138b (which defines the concave inner surface of transport cavity 140) is pulled proximally in the direction of arrow "P" (see FIG. 8A). The amount of vacuum applied and, thus, the position of outer layer 138b and, correspondingly, the volume defined by transport cavity 140, may be set based on the size of the Gestational sac "G" and/or an amount of encapsulation desired. That is, gestational sac "G" may be fully received within the internal volume of transport cavity 140 or may be partially received therein, e.g., with 50%, 65%, 80%, etc. of the volume of gestational sac "G" disposed within the internal volume of transport cavity 140.

Figure 9:
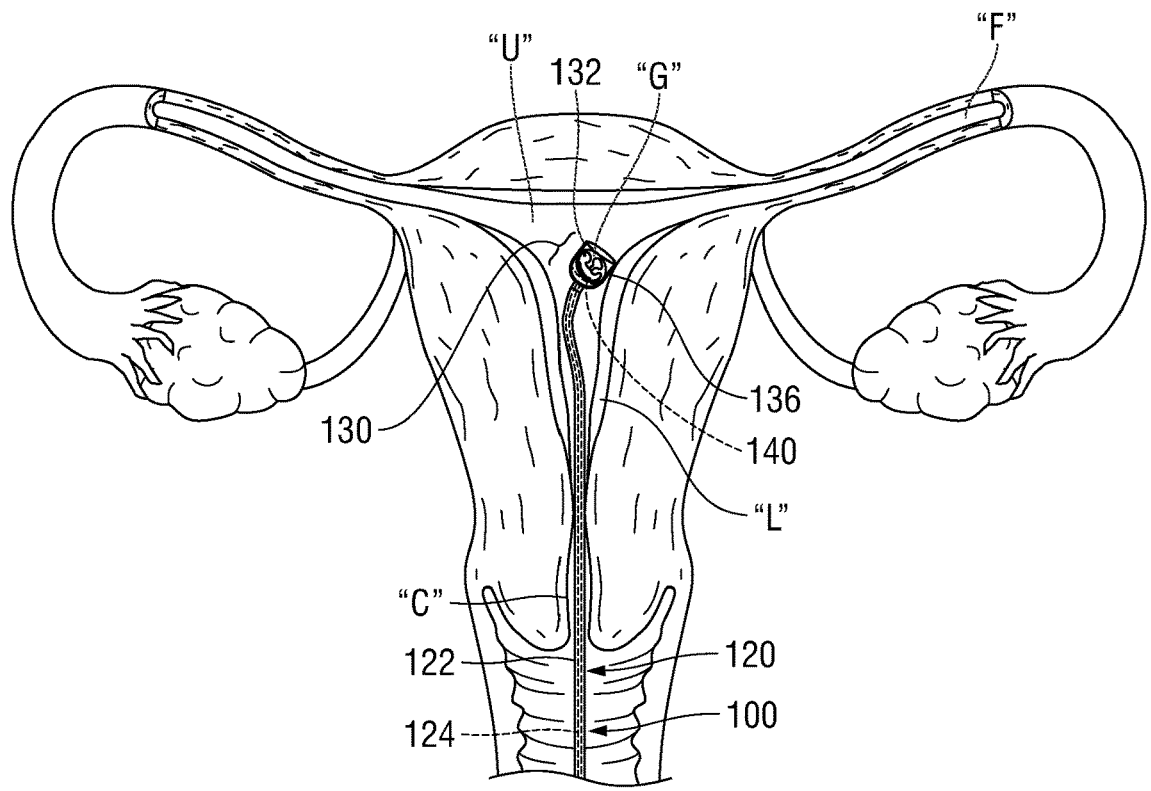
FIG. 9 is an illustration of the ectopic pregnancy treatment device of FIG. 3 positioned with the uterus to relocate the captured gestational sac, including the embryo, to the endometrial lining of the uterus.

With reference to FIG. 9, in conjunction with FIGS. 3-5, with the gestational sac "G" atraumatically received and retained at least partially within transport cavity 140 of frame 132 of end effector assembly 130, device 100 is manipulated, e.g., partially withdrawn or otherwise manipulated, such that end effector assembly 130 is pulled proximally through the fallopian tube "F" and into the uterus "U" to a suitable position adjacent the endometrial lining "L" of the uterus "U." Transport cavity 140 protects the gestational sac "G" during transport to the uterus "U," including urging through smaller-diameter openings, navigation along tortuous paths, etc. Once this position is achieved, the vacuum is released, in a controlled manner, to atraumatically release the gestational sac "G" from transport cavity 140. More specifically, upon the release of vacuum, the outer layer 138b of elastic jacket 136 is resiliently returned (e.g., opposite the direction "P" illustrated in FIG. 8A) distally towards a general planar configuration defining the distally-facing surface of the inverted, semi-ovoid frame 132 to thereby urge the gestational sac "G" distally from transport cavity 140 and towards the endometrial lining "L" of the uterus "U." If required, the desired implantation location on the endometrial lining "L" of the uterus "U" may be prepared prior to release of the gestational sac "G" and/or one or both of the gestational sac "G" and the endometrial lining "L" may be treated after release to facilitate implantation.

Figure 10:
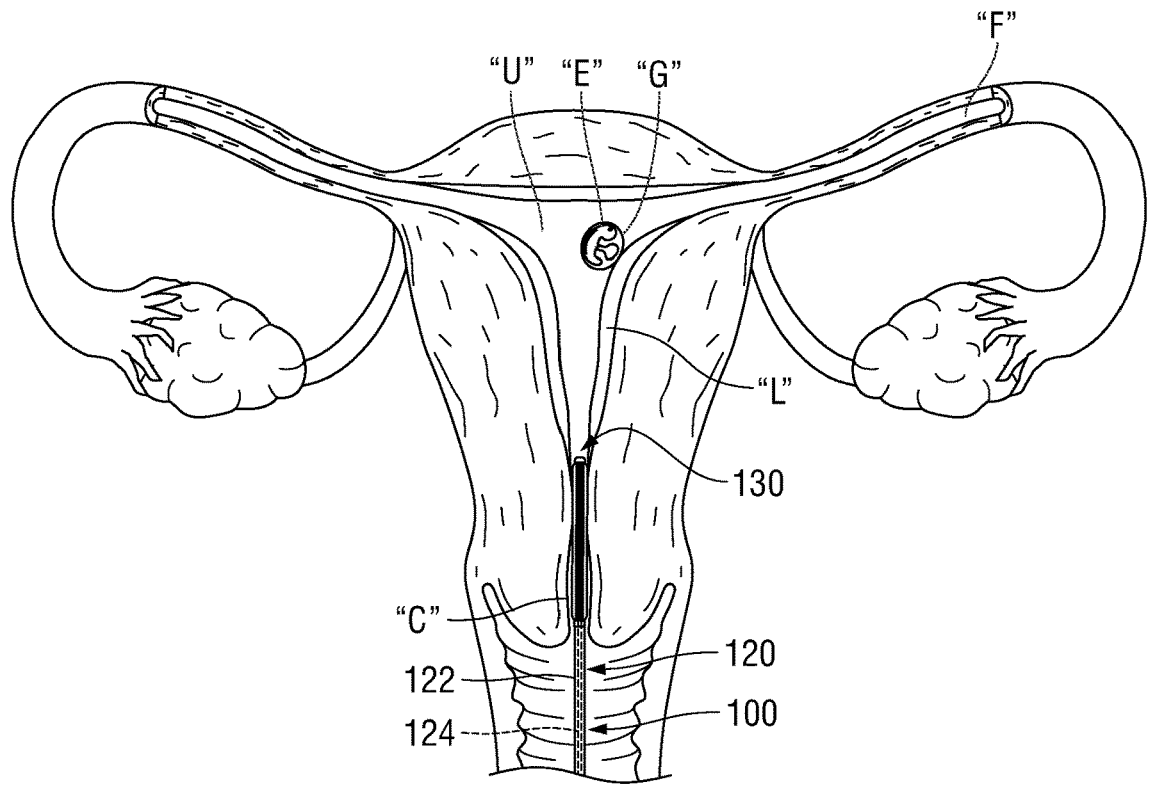
FIG. 10 is an illustration of the ectopic pregnancy treatment device of FIG. 3 being withdrawn from the uterus of a pregnant female after relocation of the gestational sac, including the embryo, to the endometrial lining of the uterus.

Referring to FIG. 10, in conjunction with FIGS. 3-5, with the gestational sac "G" properly positioned for implantation of the embryo "E" therein within the endometrial lining "L" of the uterus "U," end effector assembly 130 is returned to the collapsed condition and device 100 is removed from the uterus "U" and trans-vaginally withdrawn from the patient.

Turning to FIGS. 11 and 12, another embodiment of an ectopic pregnancy treatment device provided in accordance with the present disclosure is shown identified by reference numeral 200. Device 200 generally includes a control assembly (not shown, similar to and including any or all of the features of control assembly 110 of device 100 (FIGS. 3-5)), a shaft assembly 220 extending distally from the control assembly, and an end effector assembly 230. The control assembly may further include or be adapted to connect to a vacuum source (not shown, similar to vacuum source 116 (FIGS. 3-5)).

Shaft assembly 220 includes an outer sheath 222, an inner actuation shaft 224, and an elastic jacket 226. Outer sheath 222 may be at least partially articulable, similarly as detailed above with respect to outer support shaft 122 of device 100 (FIGS. 3-5). Outer sheath 222 defines an internal lumen 228 adapted to connect to the vacuum source to enable the application of suction through internal lumen 228. Elastic jacket 226 is disposed about a distal end portion of outer sheath 222 and extends about the distal end thereof, covering open distal end of internal lumen 228. Elastic jacket 226 is sealed about the periphery of outer sheath 222 at a position proximally-spaced from the distal end of outer sheath 222 via a collet 227 or other suitable securement mechanism. Inner actuation shaft 224 is slidably disposed within outer sheath 222 to enable transition of end effector assembly 230 between a collapsed condition (FIG. 11) and an expanded condition (FIG. 12). Alternatively, or additionally, outer sheath 222 may be configured to slide about inner actuation shaft 224 between the collapsed condition (FIG. 11) and the expanded condition (FIG. 12).

Continuing with reference to FIGS. 11 and 12, end effector assembly 230 includes an expandable frame 232 formed from a plurality of petals 234 arranged to define a conical configuration in an expanded condition thereof; other suitable expandable frames 232 are also contemplated. Frame 232 is fixed at its proximal end portion 235 to a distal end portion 225 of inner actuation shaft 224. In this manner, distal actuation of inner actuation shaft 224 relative to outer sheath 222 translates frame 232 relative to outer sheath 222 from the collapsed condition (FIG. 11) to the expanded condition (FIG. 12). In the collapsed condition, petals 234 are disposed within outer sheath 222 which resiliently retains petals 234 in a minimum-diameter condition (see FIG. 11); in the expanded condition, petals 234 extend distally from outer sheath 222 and are biased radially outwardly to achieve a conical configuration having a proximally-disposed apex, a distally-disposed base, and a maximum diameter (at least at the base) that is greater than the diameter of outer sheath 222 (see FIG. 12).

In the expanded condition, as shown in FIG. 12, the outward radial extension of petals 234 stretches elastic jacket 226 to likewise expand radially outwardly. In this condition, a portion of elastic jacket 226 extends about and defines a generally planar, distally-facing surface of the conical-shaped frame 232. Thus, similarly as detailed above, upon application of vacuum through outer sheath 222, negative pressure is established within the interior volume defined within elastic jacket 226 to pull the portion of elastic jacket 226 that previously defined the generally planar, distally-facing surface of the conical-shaped frame 232 into frame 232 to define a transport cavity (not shown, similar to transport cavity 140 (FIG. 5)) having a conical shape (with the portion of elastic jacket 226 defining the conical inner surface of the transport cavity). The amount of vacuum applied and/or the extent of expansion of frame 232 may be varied, as required, to define a suitable configuration, e.g., maximum diameter, height, height to max diameter ratio, etc., of the transport cavity for atraumatic receipt, retention, and protection of a gestational sac "G" (FIG. 2) therein.

Device 200 may be utilized similarly as detailed above with respect to device 100 to enable the atraumatic capture, transport, and release of a gestational sac "G" from a location within a fallopian tube "F" to a location within the uterus "U" adjacent the endometrial lining "L" to enable implantation and continued growth of the embryo "E" as the pregnancy progresses (see FIGS. 6-10).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;
    atraumatically capturing the gestational sac with the surgical device;
    atraumatically moving the surgical device to relocate the captured gestational sac to a position within the uterus;
    atraumatically releasing the gestational sac from the surgical device within the uterus; and
    withdrawing the surgical device,
    wherein atraumatically capturing the gestational sac includes partially retaining the gestational sac within a transport cavity defined within the surgical device.

2. The method according to claim 1, wherein the position outside the uterus is within a fallopian tube and:
    inserting the surgical device trans-vaginally includes inserting the portion of the surgical device through the uterus and into the fallopian tube; and
    atraumatically moving the surgical device includes moving the portion of the surgical device from the fallopian tube into the uterus.

3. The method according to claim 1, wherein atraumatically releasing the gestational sac from the surgical device within the uterus includes releasing the gestational sac towards an endometrial lining of the uterus.

4. The method according to claim 1, wherein atraumatically releasing the gestational sac from the surgical device within the uterus includes urging the gestational sac into contact with an endometrial lining of the uterus.

5. The method according to claim 1, wherein atraumatically capturing the gestational sac includes fully retaining the gestational sac within a transport cavity defined within the surgical device.

6. The method according to claim 1, wherein, after inserting the surgical device and prior to atraumatically capturing the gestational sac, the method includes:
    transitioning the surgical device from a collapsed condition to an at least partially expanded condition.

7. The method according to claim 6, wherein, after atraumatically releasing the gestational sac and before withdrawing the surgical device, the method includes:
    transitioning the surgical device from the at least partially expanded condition to the collapsed condition.

8. The method according to claim 1, wherein, after inserting the surgical device and prior to atraumatically capturing the gestational sac, the method includes:
    transitioning the surgical device from a collapsed condition to an expanded, at least partially inverted condition.

9. The method according to claim 8, wherein, after atraumatically releasing the gestational sac and before withdrawing the surgical device, the method includes:
    transitioning the surgical device from the expanded, at least partially inverted condition to the collapsed condition.

10. The method according to claim 1, wherein atraumatically capturing the gestational sac is facilitated via generating a vacuum within a portion of the surgical device by a vacuum source.

11. The method according to claim 1, wherein atraumatically releasing the gestational sac is facilitated by releasing a vacuum from a portion of the surgical device.

12. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;
    atraumatically capturing the gestational sac with the surgical device and fully retaining the gestational sac within a transport cavity defined within the surgical device;
    atraumatically moving the surgical device to relocate the captured gestational sac to a position within the uterus;
    atraumatically releasing the gestational sac from the surgical device within the uterus; and
    withdrawing the surgical device.

13. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;
    transitioning the surgical device from a collapsed condition to an at least partially expanded condition;
    atraumatically capturing the gestational sac with the surgical device;
    atraumatically moving the surgical device to relocate the captured gestational sac to a position within the uterus;
    atraumatically releasing the gestational sac from the surgical device within the uterus; and
    withdrawing the surgical device.

14. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;
    transitioning the surgical device from a collapsed condition to an expanded, at least partially inverted condition;
    atraumatically capturing the gestational sac with the surgical device;
    atraumatically moving the surgical device to relocate the captured gestational sac to a position within the uterus;
    atraumatically releasing the gestational sac from the surgical device within the uterus; and
    withdrawing the surgical device.

15. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;
    atraumatically capturing the gestational sac with the surgical device by generating a vacuum within a portion of the surgical device by a vacuum source;
    atraumatically moving the surgical device to relocate the captured gestational sac to a position within the uterus;
    atraumatically releasing the gestational sac from the surgical device within the uterus; and
    withdrawing the surgical device.

16. A method of treating an ectopic pregnancy without compromising the pregnancy, comprising:
    inserting a surgical device trans-vaginally to a position outside a uterus such that a portion of the surgical device is positioned adjacent a gestational sac, including an embryo, that is disposed outside the uterus;

atraumatically capturing the gestational sac with the surgical device;
atraumatically moving the surgical device to relocate the captured gestational sac to a position within the uterus;
atraumatically releasing the gestational sac from the surgical device within the uterus by releasing a vacuum from a portion of the surgical device; and
withdrawing the surgical device.

\* \* \* \* \*